United States Patent [19]

Delpy

[11] 4,274,417
[45] Jun. 23, 1981

[54] INSTRUMENTS FOR USE IN THE MEASUREMENT OF GASES IN BODY FLUIDS

[75] Inventor: David T. Delpy, London, England

[73] Assignee: National Research Development Corporation, London, England

[21] Appl. No.: 76,724

[22] Filed: Sep. 18, 1979

[30] Foreign Application Priority Data

Sep. 22, 1978 [GB] United Kingdom ............... 37801/78

[51] Int. Cl.³ .............................................. A61B 5/00
[52] U.S. Cl. .................................... 128/632; 128/348
[58] Field of Search ......................... 128/632, 635, 348

[56] References Cited

U.S. PATENT DOCUMENTS

| | | | |
|---|---|---|---|
| 3,572,315 | 3/1971 | Cullen | 128/632 |
| 3,658,053 | 4/1972 | Fergusson et al. | 128/632 |
| 3,952,730 | 4/1976 | Key | 128/632 |

FOREIGN PATENT DOCUMENTS

| | | | |
|---|---|---|---|
| 965878 | 8/1964 | United Kingdom | 128/350 R |
| 1494474 | 12/1977 | United Kingdom | 128/632 |
| 2017499 | 10/1979 | United Kingdom | 128/349 R |

OTHER PUBLICATIONS

Key, "A Flexible Catheter . . . Tensions", Med. & Biol. Eng., vol. 13, No. 4, p. 583, Jul. 1975.
Wald et al., "Cont. Measurement . . . Spectrography", Med. & Biol. Eng., vol. 8, pp. 111–128, 1970.
Massaro et al., "Non-Polarographic Blood Gas . . .", Bio-Mat, pp. 385–396. 1976.

Primary Examiner—Lee S. Cohen
Attorney, Agent, or Firm—Cushman, Darby & Cushman

[57] ABSTRACT

An instrument for use in the measurement of gases in body fluids comprises a flexible catheter having an inner tube within an outer tube, the tubes being of such diameters that there is a substantially cylindrical passage between the tubes which can be evacuated or flushed with a non-interfering gas. Spacers can be provided in the passage, such as radial webs or a single or double helix filament.

6 Claims, 5 Drawing Figures

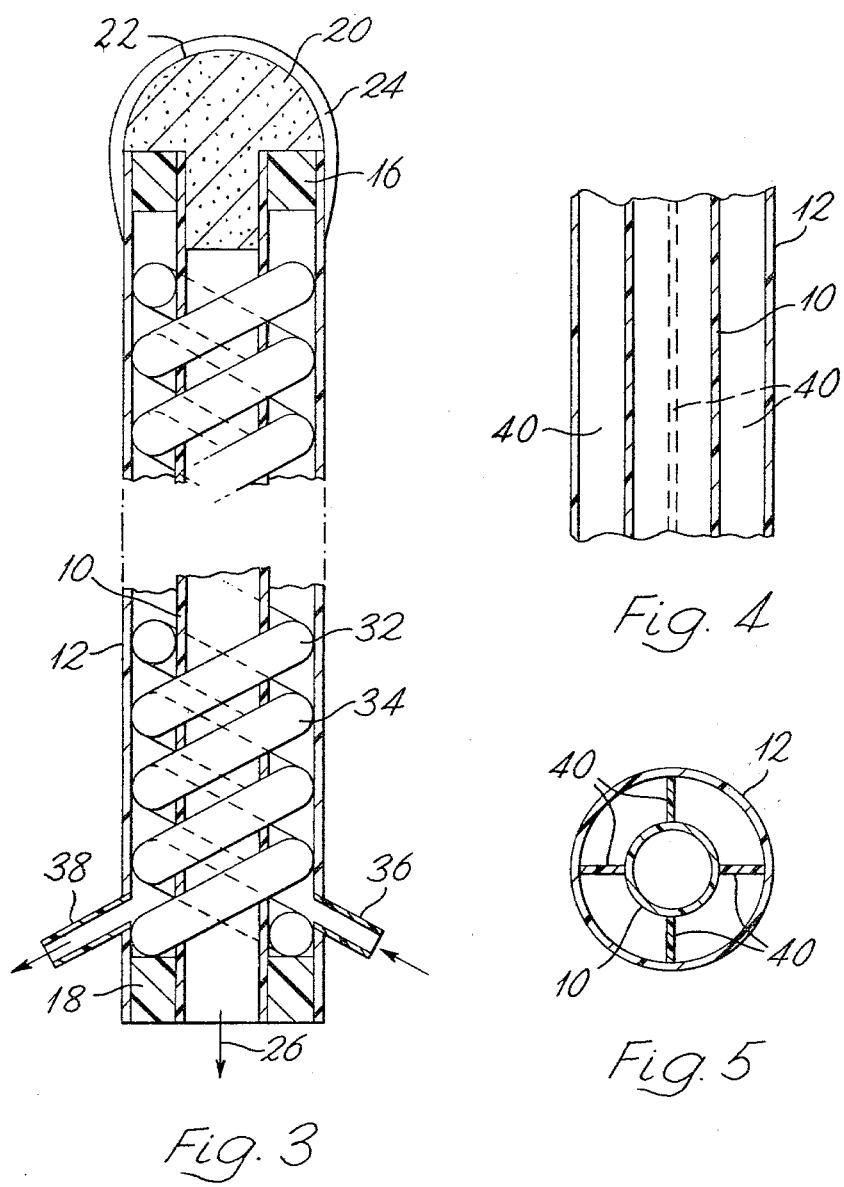

INSTRUMENTS FOR USE IN THE MEASUREMENT OF GASES IN BODY FLUIDS

It is a frequent medical requirement to measure at a remote instrument the concentration of gases dissolved in body fluids; one example is the measurement of blood gases. When the in vivo measurement of blood gases is made continuously, it is conventional to use an instrument in the form of a catheter which is substantially impermeable to gases and whose distal end is closed by a gas-permeable membrane. The instrument is inserted into the relevant blood vessel and its interior is connected under vacuum to the inlet port of a mass spectrometer. Gases dissolved in the blood diffuse through the membrane and pass along the catheter to the mass spectrometer in which they are analysed.

It is convenient if the catheter tube is flexible allowing it to be guided to a required sampling site within a blood vessel. However, the gas permeability of the wall of the flexible tube is so high that gas diffusion through the wall represents an appreciable percentage of the total gas reaching the mass spectrometer with consequential errors when it is assumed in calculations that all gas passes through the gas-permeable membrane.

In general, plastics materials which have low gas permeability are relatively rigid, and those which have high gas permeability are relatively flexible. While some degree of stiffness may be tolerable in an adult, catheters for use in small children and babies must be very flexible, and therefore the error caused by gas diffusion is greatest.

According to the invention, an instrument for use in the measurement of gases in body fluids comprises a flexible catheter having an inner tube within an outer tube, the tubes being of such diameters that there is a substantially cylindrical passage between the tubes; sealing means to seal the cylindrical passage at each end of the catheter; at one end of the catheter a gas permeable closure covering the end of the inner tube; and at the other end of the catheter connection means to allow connection of the cylindrical passage to a gas flow system and connection of the inner tube to a gas analysis apparatus.

In use, the cylindrical passage may be evacuated, while the inner tube is connected separately under vacuum to the inlet port of analysis apparatus such as a mass spectrometer. Alternatively, the cylindrical passage may be continuously flushed with a gas which will not affect the measurement being made by the gas analysis apparatus.

In some embodiments there is further provided spacing means to space the inner tube from the outer tube while maintaining between the tubes at least one continuous passage extending the length of the catheter.

In one embodiment the spacing means comprises a plurality of webs of material extending radially between the inner and outer tubes for substantially the whole length of the catheter.

In another embodiment the spacing means comprises means such as a filament arranged as a helix in the cylindrical passage and in contact with both the inner and outer tubes. Either a single or a double helix may be used, providing respectively one and two helical passages the length of the catheter.

An instrument having any arrangement of spacing means, or an instrument which has no spacing means, can be used in conjunction with means to evacuate the space between the inner and outer tubes.

For use with a gas flushing arrangement, either the double helix spacing means can be used, such a spacing means defining two helical paths, with gas travelling in one direction along the catheter in one of the paths, and returning along the other. Alternatively, radial webs may provide a number of straight paths, the connections being such that gas travels in one direction along the catheter in one or more of the paths, and returns along another or other paths. Clearly, the spacing means must be arranged with apertures so that, near the distal end, gas can pass from one flow path to the other.

An instrument according to the invention can be used for many measurements of gas dissolved in a body fluid, but a particular application is in blood gas analysis, when the instrument may utilize the arrangement described in the Specification of U.K. Pat. No. 1,494,474, in which there is provided at the distal end a rigid porous body secured in the end of the inner tube and having a smoothly rounded portion projecting from said end and a sheath of a non-thrombogenic polymeric material part of which fits closely around the outer tube of the catheter and part of which covers the projecting portion of the porous body and constitutes the gas-permeable membrane.

The invention will now be described by way of example only with reference to the accompanying drawings in which:

FIG. 3 is a longitudinal section through a third embodiment; and

FIGS. 4 and 5 are respectively longitudinal and tranverse sections through a part of a fourth embodiment.

Figure 1:
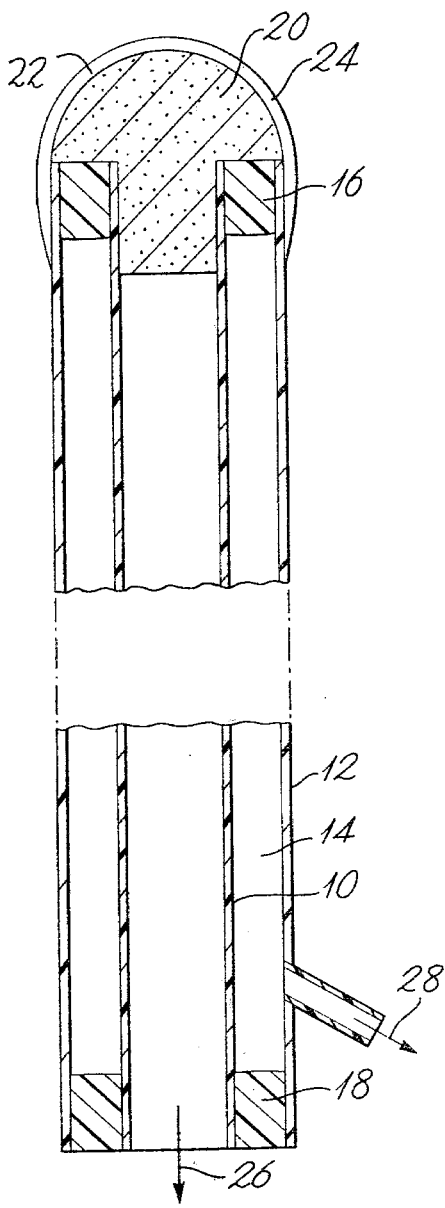
FIG. 1 is a longitudinal section through a first embodiment of blood gas analysis instrument.

In FIG. 1 an instrument according to the invention suitable for use in blood gas analysis comprises an inner tube 10 and an outer tube 12, both of a flexible plastics material such as polyvinylchloride. Typically the external diameter of the outer tube 12 is less than 1.5 millimeters. There is an annular gap 14 between the tubes and this gap is sealed by epoxy resin seals 16, 18 at respectively the distal and proximal ends.

At the distal end a porous plug 20 of a material such as sintered bronze is held in the end of the inner tube and extends beyond the ends of both tubes as a substantially hemispherical surface 22 which is covered by a layer 24 of gas permeable material, such as silicone rubber about 75 microns thick; the layer covers the porous plug and extends down the outside of the outer tube 12 to which it is sealed.

At the proximal end, the inner tube 10 is connected to a gas detection apparatus, such as a mass spectrometer, as indicated by the arrow 26. The annular gap 14 is connected to a vacuum pump, as indicated by the arrow 28. In use, the distal end is inserted into an artery, and gas from the blood which passes through the permeable membrane 24 and plug 20 is pumped along the inner tube 10 to a mass spectrometer or other analysis instrument. Any gas from the blood which passes through the walls of the outer tube 22 is pumped away and does not affect the measuring instrument. Allowances can be made by calibration for gas diffusing through the inner tube into the annular gap 14. The risk of diffusion from the outer to the inner tube is higher in this embodiment than in the alternatives described below because when the tubes are bent, the outer and inner tubes may come into contact with one another.

Figure 2:
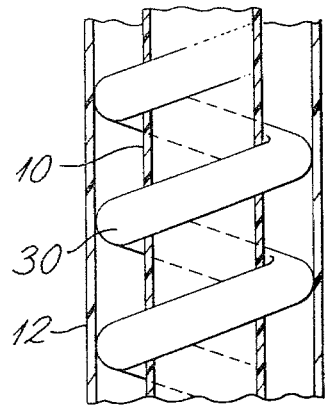
FIG. 2 is a longitudinal section through a part of a second embodiment.

The embodiment illustrated in FIG. 2 overcomes this problem. Between the inner and outer tubes 10 and 12 there is a filament 30 arranged as a helix in the gap 14. The filament is of such a diameter as to be in contact with both the outer and the inner tubes, and its presence ensures that the inner tube remains concentric with the outer tube. The connections at the proximal end of the tubes 10 and 12 will be as described with reference to FIG. 1.

In FIG. 3, the annular gap 14 between the tubes is occupied by two filaments 32, 34, arranged as a double helix; two helical passages therefore extend between the distal and proximal ends of the instrument. At the distal end, the filaments terminate at a position spaced from the seal 16 so that the ends of the two helical passages are in connection. At the proximal end, a gas inlet tube 36 is connected to the outer tube so as to coincide with one helical passage, and a gas outlet tube 38 coincides with the other helical passage.

In use, a flushing gas is pumped through inlet tube 36, passes along one helical passage to the distal end of the catheter and returns along the other helical passage to the outlet tube. Any gas diffusing into the gap is carried away by the flushing gas. The gas is chosen so as not to affect measurement of any blood gases passing along the inner tube.

An alternative embodiment, suitable for use with a gas flushing system, is shown in FIGS. 4 and 5. The tubes 10, 12, are spaced by four radial webs 40 which can be formed integrally with the outer and inner tubes during the tube extrusion process. Of the four longitudinal gaps, two can be connected to a gas inlet tube and two to a gas outlet tube.

The embodiments shown in FIGS. 3, 4 and 5 can also be used in conjunction with a vacuum arrangement to remove gas from the annular gap 14.

The instrument according to the invention can in one arrangement be connected to a permanent tube connection which in turn is connected to a mass spectrometer. Alternatively, the instrument can be of greater length than is conventional e.g. 2 or 3 meters, when the proximal end can be connected directly to the mass spectrometer. The instrument can, if required, be disposable after use.

While the embodiments of FIGS. 1 and 3 show a particular arrangement for allowing gas diffusion through a permeable membrane at the distal end, the invention can be used in combination with any other suitable membrane arrangement.

I claim:

1. An instrument for use in the measurement of gases in body fluids comprising a flexible catheter having an inner tube within an outer tube, the tubes being of such diameters that there is a substantially cylindrical passage between the tubes; sealing means to seal the cylindrical passage at each end of the catheter; at one end of the catheter a gas permeable closure covering one end of the inner tube, and at the other end of the catheter first connection means to allow connection of the cylindrical passage to a gas flow system and second connection means to allow connection of the inner tube to a gas analysis apparatus.

2. An instrument according to claim 1 further comprising spacing means in the cylindrical passage to space the inner tube from the outer tube while allowing within the cylindrical passage at least one continuous path extending the length of the catheter.

3. An instrument according to claim 2 in which the spacing means comprises a plurality of webs of material extending radially between the inner and outer tubes substantially the whole length of the catheter.

4. An instrument according to claim 2 in which the spacing means comprises filament means arranged as a helix in the cylindrical passage and in contact with both the inner and outer tubes.

5. An instrument according to claim 2 in which the spacing means comprises two filament means arranged as a double helix in the cylindrical passage, each in contact with both the inner and outer tubes.

6. An instrument according to claim 1 in which the gas permeable closure comprises a rigid porous body secured in said one end of the inner tube and having a smoothly rounded projection from said one end; and a sheath of a non-thrombogenic polymeric material part of which fits closely around the outer tube of the catheter and part of which covers the projection portion of the porous body and which constitutes the gas permeable closure.

* * * * *